(12) United States Patent
Li et al.

(10) Patent No.: US 8,290,597 B2
(45) Date of Patent: Oct. 16, 2012

(54) SIGNAL PROCESSING IN DEVICES, FOR USE WITH A DEFICIENT SIGNAL-RESPONSIVE BODY PART

(75) Inventors: Guoping Li, Southampton (GB); Mark Edward Lutman, Romsey (GB)

(73) Assignee: University of Southampton, Southampton, Hants (GB)

( * ) Notice: Subject to any disclaimer, the term of this patent is extended or adjusted under 35 U.S.C. 154(b) by 147 days.

(21) Appl. No.: 12/676,556

(22) PCT Filed: Sep. 5, 2008

(86) PCT No.: PCT/GB2008/002993
§ 371 (c)(1),
(2), (4) Date: Jun. 2, 2010

(87) PCT Pub. No.: WO2009/030909
PCT Pub. Date: Mar. 12, 2009

(65) Prior Publication Data
US 2010/0241193 A1    Sep. 23, 2010

(30) Foreign Application Priority Data

Sep. 5, 2007 (GB) .................................. 0717210.9
Aug. 27, 2008 (GB) .................................. 0815573.1

(51) Int. Cl.
*A61N 1/18* (2006.01)
(52) U.S. Cl. .......................................................... 607/55
(58) Field of Classification Search ............... 607/55–57
See application file for complete search history.

(56) References Cited

U.S. PATENT DOCUMENTS

| 6,755,530 B1 | 6/2004 | Loftus |
| 2006/0253164 A1 | 11/2006 | Zhang et al. |
| 2007/0081683 A1 | 4/2007 | Carney |

FOREIGN PATENT DOCUMENTS
WO    WO 2007/075477 A    7/2005

OTHER PUBLICATIONS

Gilley et al "Minimization of cochlear implant stimulus artifact in cortical auditory evoked potentials" Clinical Neurophysiology, Elsevier Science, vol. 117, No. 8 Aug. 1, 2006 (12 pages).
Hyvärinen Aapo et al. "Statistical model of natural stimuli predicts edge-like pooling of spatial frequency channels in V2" BMC Neuroscience, Biomed Central, vol. 6, No. 1, Feb. 16, 2005 (12 pages).

*Primary Examiner* — Scott Getzow
*Assistant Examiner* — Amanda Patton
(74) *Attorney, Agent, or Firm* — Flaster/Greenberg, P.C.

(57) ABSTRACT

A cochlear implant provides electrical pulses to neurons and is configured to convert the excitation signal into a sparsified signal for electrically stimulating the neurons, thereby reducing the redundancy of the stimuli applied to the neurons. A signal analyser is configured to perform dimension reduction or factorisation of said excitation signal in the time domain or in the frequency domain followed by a sparse transform, the resulting relatively clean output signal providing the input to an inverse transformation step to create the sparsified signal. The dimension reduction or factorisation can be performed by principal component analysis (PCA), and the sparse transform can be performed by independent component analysis (ICA).

12 Claims, 7 Drawing Sheets

Fig. 7  Spectrum envelope of sparse stimuli

Fig. 8  Sequence stimuli of sparse stimuli

Fig. 9

SIGNAL PROCESSING IN DEVICES, FOR USE WITH A DEFICIENT SIGNAL-RESPONSIVE BODY PART

The invention relates to signal processing in devices, such as a cochlear implant, for providing electrical pulses to neurons of a deficient signal-responsive body part. Such devices have a limited communication bandwidth, and the signal processing needs to be configured to utilise the available bandwidth.

A cochlear implant is a device which receives signals from one or more microphones, and processes the signals to provide electrical stimuli to neurons of the auditory nerve.

In known cochlear implants a microphone signal is fed into a filter bank, and signal envelopes are extracted based upon the power spectra of the frequency channels. An algorithm may select channels, for example 12 out of 20 available channels, to provide selected envelopes, the selection being based on the amplitudes of the channels, and the selected envelopes are transformed into sequences of electrical pulses to stimulate the neurons of the auditory nerve. The microphone (and most of the signal processing circuits) is generally mounted above the user's ear and communicates with the internal receiver/stimulator by a communications link of limited bandwidth.

The limited bandwidth of such devices occurs because of the limited number of channels, and the limited dynamic range of the device. A further limitation is the ability of neurons to encode the electrical pulses.

The limited bandwidth creates a restriction in providing suitable stimuli to the auditory nerve.

The invention arose from our investigations of ways to accommodate a limited bandwidth whilst providing sufficient stimuli to the auditory nerve.

According to the invention we provide apparatus for providing electrical pulses to neurons of a deficient signal-responsive body part in response to an incoming excitation signal having a signal spectrum to which the body part would be responsive if the body part was functioning normally, the apparatus being configured to convert the excitation signal into a sparsified signal for electrically stimulating the neurons, thereby reducing the redundancy of the stimuli applied to the neurons by the apparatus.

The present invention presents an approach that is an advance on the usual approach. Usually, approaches try to encode and send as much information as possible from the acoustical space to the electrical stimuli or use arbitrary criteria to select signal components. We have formalised the desirability of redundancy reduction and used formal statistical methods to maximise the independence of the information coded in the stimulation signal. With limited bandwidth, the redundant information in prior art devices occupies the precious resources of bandwidth, which in turn can cause less accuracy of encoding other important information. Noise is especially a problem for many cochlear implant users. One of reasons is that the noise competes for channel resources with the important information and makes other important information masked or not well coded.

Another reason to perform redundancy reduction is to consider the sparse coding principle which appears to be followed by sensory neurons. At each moment, only few neurons fire, which minimises the probabilities of neurons responding to redundant signals. We have appreciated that the stimuli should be designed in a way which obeys the physiological sparse coding principle. That is, we have appreciated the stimuli of a cochlear implant should be sparse and such that the neurons can fire sparsely.

In order to get such a sparse stimulus pattern, we first get a neuronal activity pattern by sparsifying the redundant acoustical signal. The sparse transformation can be achieved through different techniques.

The apparatus preferably comprises a signal analyser configured to perform dimension reduction or factorisation of said excitation signal in the time domain or in the frequency domain followed by a sparse transform, the resulting relatively clean output signal providing the input to an inverse transformation step to create the sparsified signal.

Said dimension reduction or factorisation may be performed by principal component analysis (PCA).

Said sparse transform may be performed by independent component analysis (ICA).

Suppose we have a clean signal X, and a linear transform W such that S=W*X makes S as sparse as possible. A zero mean random variable S is sparse when it has a super Gaussian distribution, with a peak at zero, and low tails (Hyvarinen and Oja, 1997). It is sparse since there is less activity within the representation; most elements are zeros (non-active). The sparse transform can be achieved by ICA when absence of correlation is implemented as a constraint, since the optimization of independence amounts to making the components sparsely distributed for each component. Sparse coding of sensory data has been shown to have advantages, not only physiologically but also it promotes the efficiency of coding information (Field, 1994; Barlow, 2001).

Recently, sparse coding was also used for de-noising of speech and image data (Hyvarinen, 1999; 2006; Huang, Li et al., 2006). It requires a clean data set to be trained to get the ICA transformation matrix W. We suppose that in normal sensory systems neurons encode the signal in a way so that S=W*X, where W is the sparse transform and S is the neuron activity. But due to the redundancy of X, there are still some neurons firing corresponding to the redundant parts of the signal. Also some neurons fire due to noise. But these firing activities can be assumed to be very small due to inhibition mechanisms or masking effects of neurons firing. For damaged sensory systems that do not function in this way, a threshold can be introduced artificially to reduce such small firing activity.

The ICA output signal S is preferably subject to thresholding to reduce redundant components before the resulting thresholded signal is subjected to an inversion step to create electrical pulses.

Thus we can add a threshold by defining that if the activity is below a certain level, electrical pulses should not be delivered. Therefore, the brain will not perceive these unnecessary firing neurons and will focus on the stimuli which are the most sparse representation of the input signal. Hyvarinen (Hyvarinen, 1999) discussed the general principle of how to set a threshold based on maximum likelihood optimization and some prior assumption of super Gaussian distribution of the sparse components.

This sparse thresholding can indeed be seen as a way of redundancy reduction. The redundant information can be reduced by such sparse representation. Only few neurons fire to encode a redundant signal like speech at a specific time. And so we only need to stimulate a very small set of neurons each time to encode an environmental signal.

The apparatus may use PCA to reduce the dimension of the incoming signal and then apply ICA analysis on the reduced signal.

The apparatus may use the maximum likelihood method to get the signal threshold, using a relationship of the form:

$$S\_essential = \frac{\text{sign}(S) . * \max(0, |S| - a. * \sigma^2)}{(1 + \sigma^2 * b)}$$

where S_essential corresponds to the sparse envelopes of said ICA output signal S, $\sigma^2$ is the estimated variance of the noise, a and b are selected integers, as described by Hyvarinen (1999)

In one embodiment of the invention a=3 and b=8.

The threshold parameters (a, b) in the equation may be a function of signal-noise-ratio (SNR) of S. A lower SNR may require a higher threshold. The SNR can be estimated by various methods. The parameter a can also be subject to patient choice in different environments.

Instead of arraying the PCA and ICA process after envelopes of the signals were extracted, the PCA and ICA process can also be used earlier, prior to filter banks.

The sparse coding box can be seen as

This input can be either audio signal in the time domain or the spectral amplitude in the frequency domain. For example, in the time domain:

Audio signal ⟶ PCA/ICA ⟶ Thresholding ⟶
Inverse ICA ⟶ Filter banks ⟶
Envelopes ⟶ Electrical stimuli Alternatively, the PCA/ICA can be arranged to happen immediately after filter banks before envelopes are extracted. Thus:

Audio signal→Filter banks→PCA/ICA→Thresholding→Inverse ICA→Envelopes→Electrical stimuli.

The invention will now be further described, by way of example only, with reference to the accompanying drawings in which.

REDUNDANCY REDUCTION OF SIGNAL

A signal can be seen as two parts, the most essential part to represent the original signal, and the redundant or noisy part.

$$X1 = X' + N \tag{1}$$

X' is the essential part to represent the signal X1.
N is the redundant or noisy part of the signal X1.

First, we use PCA to reduce the dimensions of the original signal, creating a transformed signal (X), containing only the main principal components (eg 8 out of 20).

$$X = PCA(X1) \tag{2}$$

We then perform a sparse transformation (W) using ICA on the relatively clean signal X:

$$S = W * X \tag{3}$$

The ICA transformation must reduce or remove redundancy in S, because the independent components are calculated to be as independent as possible. This is what is meant by a sparse representation.

The independent components of S can be expressed in order of reducing magnitude as:

$$S = S1 + S2 + S3 + \ldots Sn \tag{4}$$

We assert that the larger independent components of S are the most important parts and the smaller independent components are less important. We next remove the smaller components by applying a threshold. All components below the threshold are set to zero.

$$S - S\_threshold = S' \tag{5}$$

$$S' = S1 + S2 + S3 + \ldots St \tag{6}$$

Where St is the threshold components (t<n).

The neuron firing pattern will be simplified as S', representing the most essential parts of the signal X.

We can then perform an inverse transform on S' to obtain a signal in the stimulus domain.

$$\hat{X} = W^{-1} * S' \tag{7}$$

$\hat{X}$ then contains the most essential parts of X, which should be used to generate the electrical pulse sequence for cochlear implant stimuli.

The maximum likelihood method can be used to get the S' (Hyvarinen, 1999). If we assume the distribution of essential components of S is super-gaussian, and distribution of the redundant parts is gaussian.

We are then able to estimate essential components given S. The maximum likelihood method gives the following estimator for essential parts (Hyvarinen, 1999):

$$S\_essential = \frac{\text{sign}(S) . * \max(0, |S| - a. * \sigma^2)}{(1 + \sigma^2 * b)} \tag{8}$$

Figure 2:
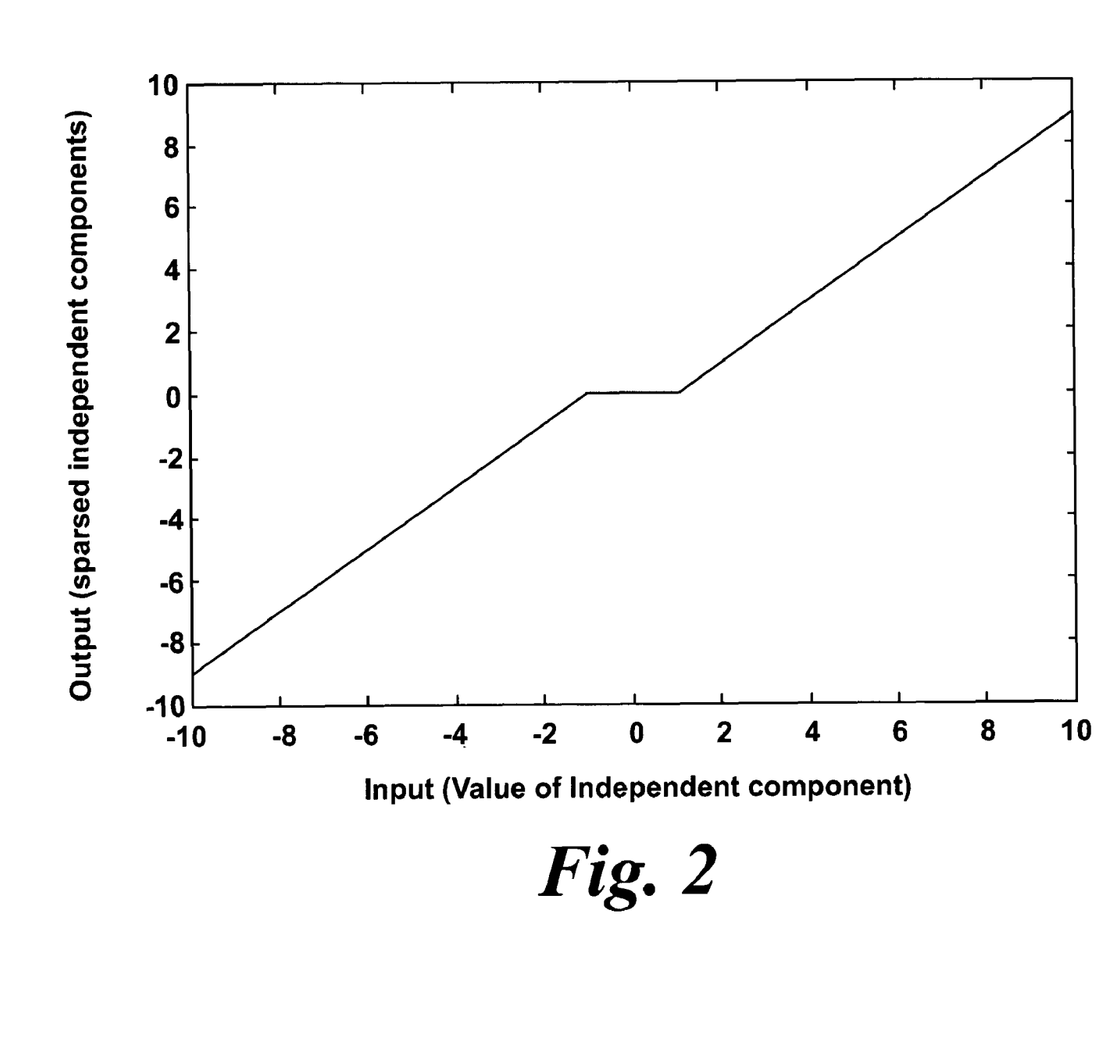
FIG. 2 shows a thresholding function applied on the independent components.
Figure 3:
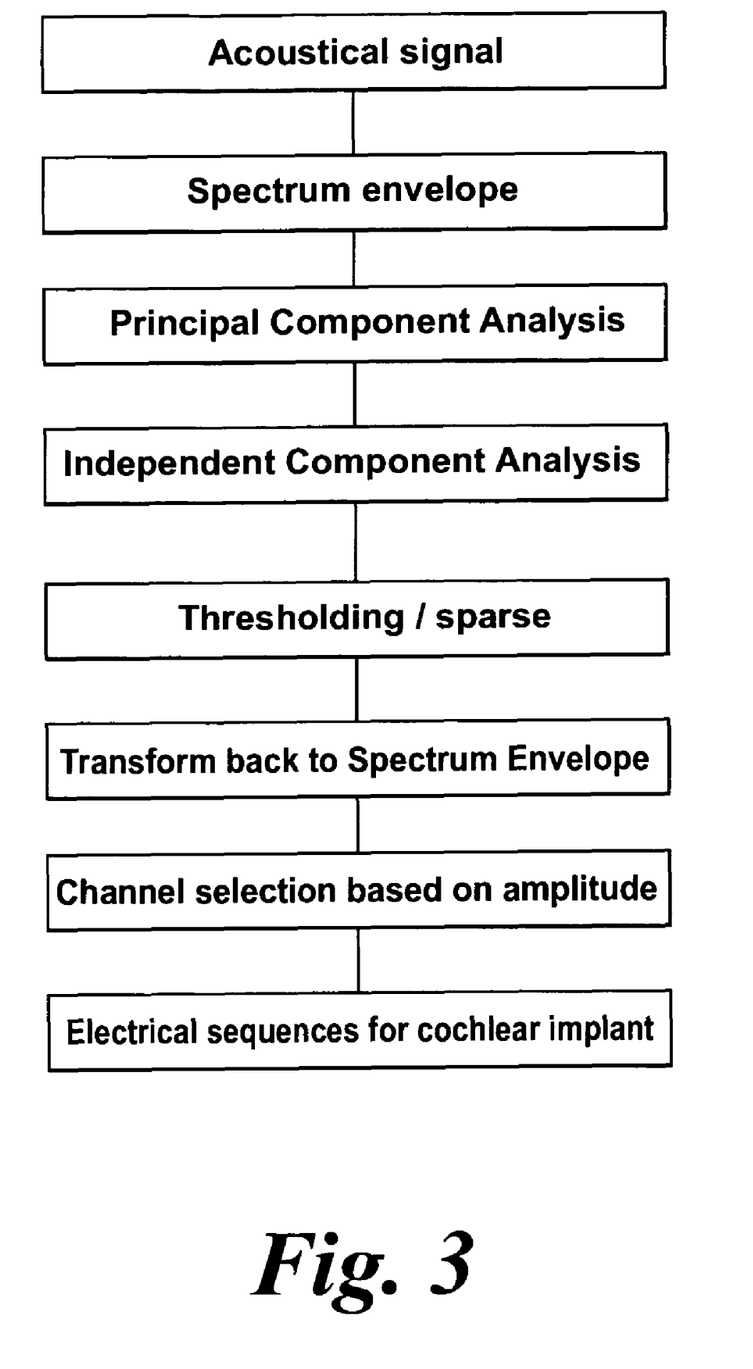
FIG. 3 is a flow diagram of the signal process steps to generate sparse stimuli in a cochlear implant in accordance with the invention.
Figure 4:
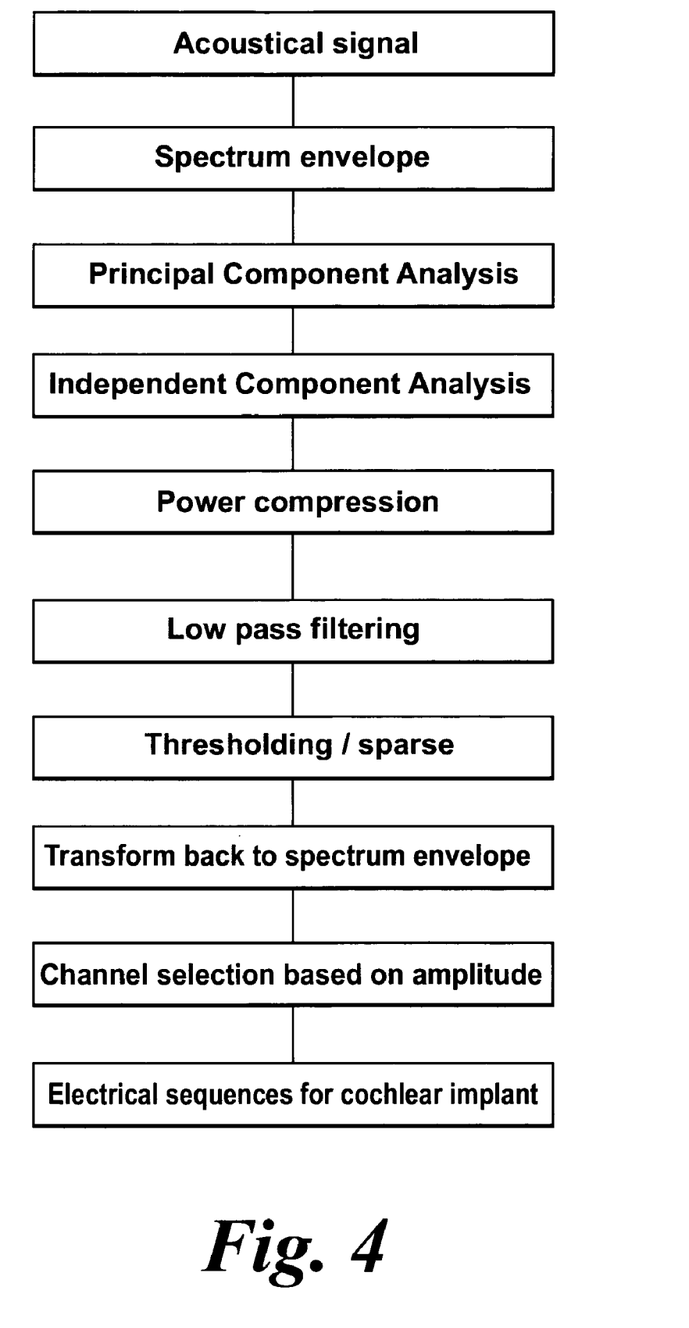
FIG. 4 is a block diagram similar to FIG. 1 showing a modification employing thresholding of the output of the ICA.
Figure 5:
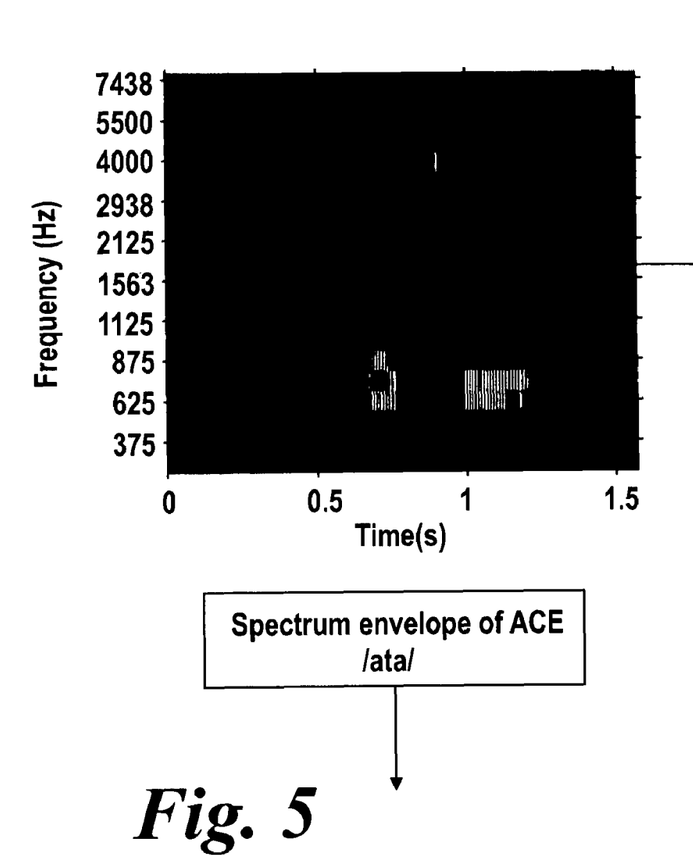
FIG. 5 shows, for comparison purposes, the spectrum envelope of an acoustic signal that has been processed by a conventional ACE algorithm, in a prior art cochlear implant.
Figure 6:
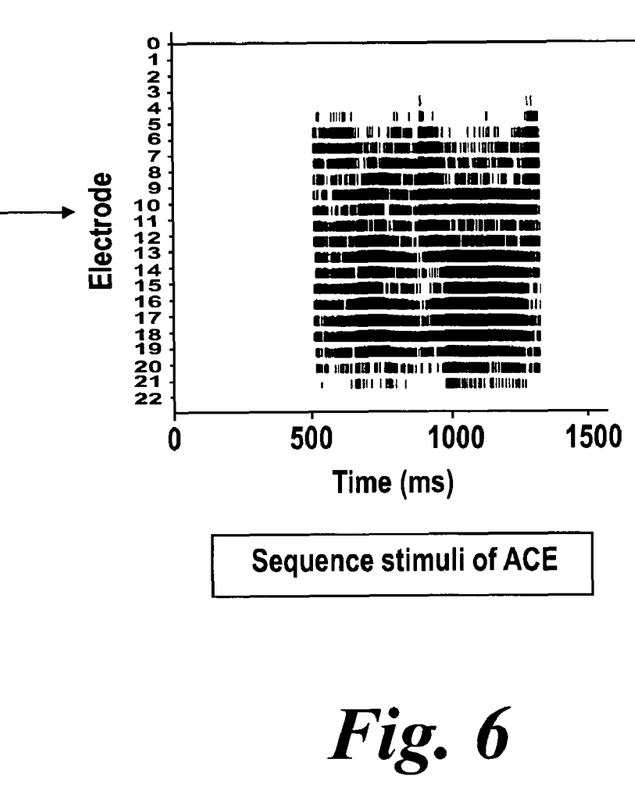
FIG. 6 shows the pulse stimuli for application to the auditory nerve and produced by convolving the signals of FIG. 5 with pulses.
Figure 7:
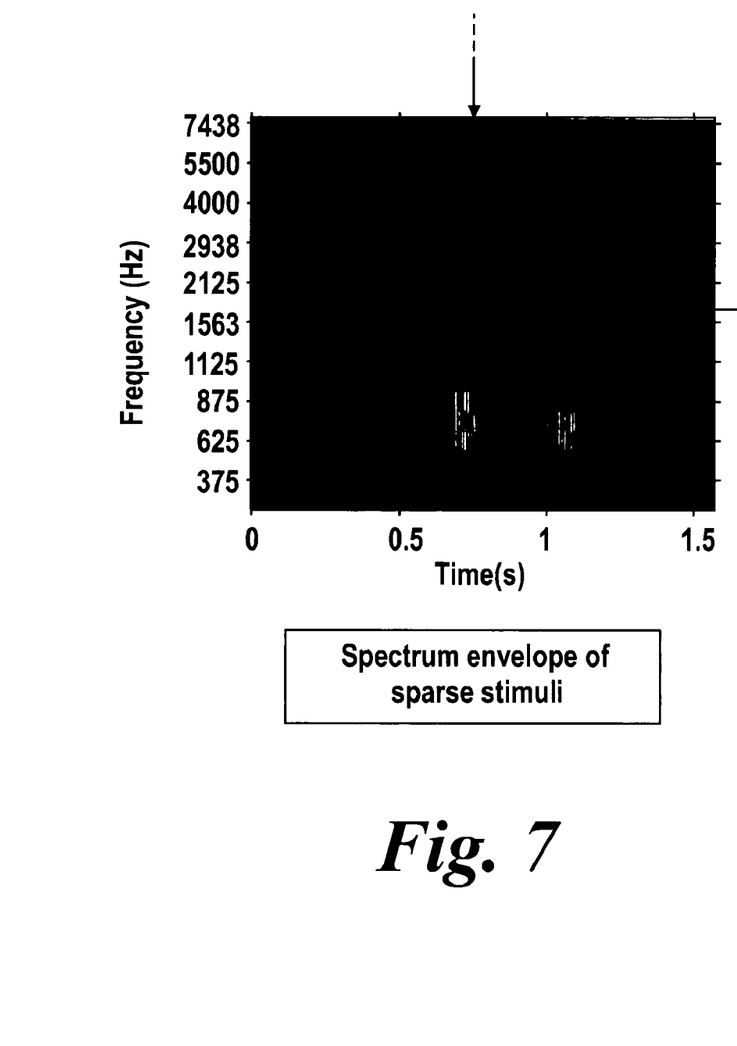
FIG. 7 shows the spectrum envelope of an acoustic signal that has been processed by a cochlear implant in accordance with the invention using the signal processing of FIG. 1.
Figure 8:
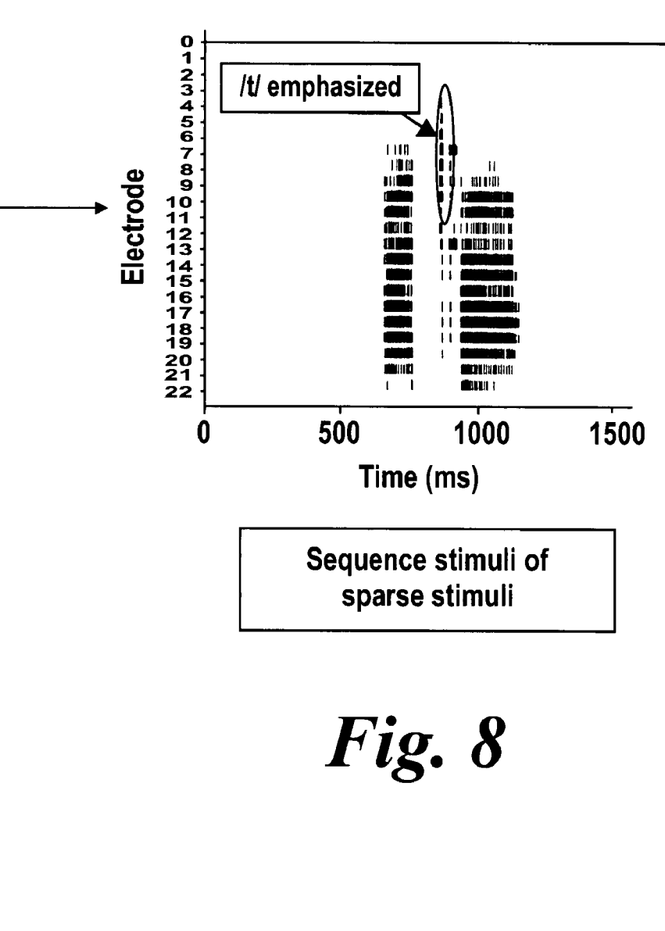
FIG. 8 shows the pulse stimuli for application to the auditory nerve and produced by convolving the signals of FIG. 7 with pulses.

$\sigma^2$ is the variance of the noise, which needs to be estimated. Here for simplicity, we use variance of S to approximate the variance of redundant or noisy parts, and our results shows it is a reasonable approximation. We choose a=3 and b=8 from experimental trials. The nonlinear threshold function is plotted in FIG. 2.

Although there might be difficulties for convergence of ICA in noisy conditions (Davies, 2004), we find in practice the algorithm can always converge after the PCA process for our experimental signals at signal-to-noise ratios: 0, 5, 10 and 15 dB.

Cochlear Implant Signal Processing Scheme

Figure 1:
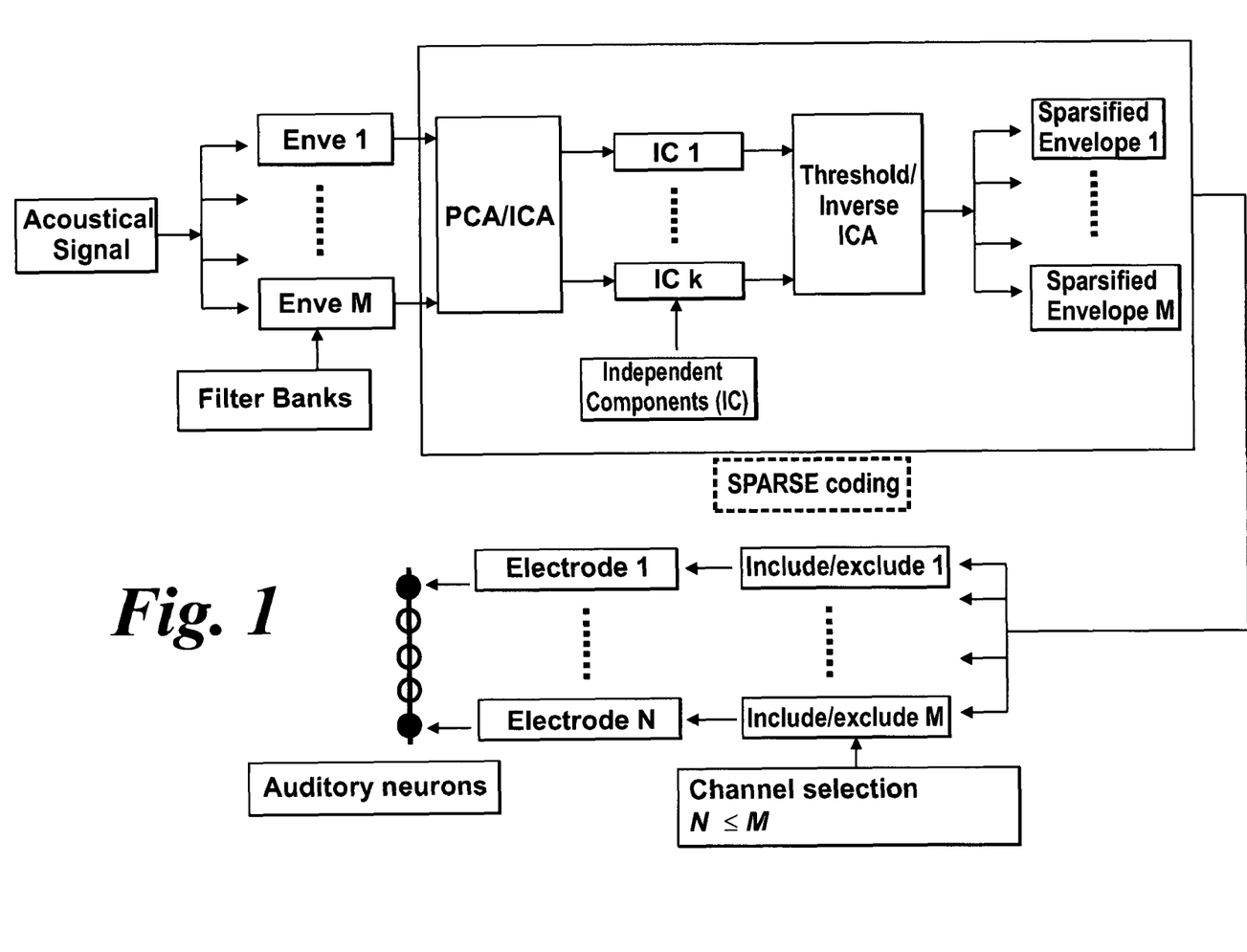
FIG. 1 is a block diagram of the signal processing stages performed by a cochlear implant in accordance with the invention.

With reference to FIG. 1, an acoustic signal X1 from one or more microphones is subjected to a bank of filters that divide the signal into M frequency bands, and the envelopes Enve1-M of the frequency bands are fed as M channels to a PCA/ICA element which outputs a series of k sparsely coded Independent Components $IC_{1-k}$. The number of dimensions has been reduced here from M to K. The sparsely coded signals $IC_{1-k}$ are then thresholded and re-converted to the frequency domain by the Threshold/Inverse ICA element TI to provide a series of M sparsified envelopes SE1-M.

A selection N of the M envelopes, chosen by a selection process, is convolved with pulses, and the resulting pulse sequences are fed to respective electrodes EL1-N which stimulate the auditory neurons NEU. Various selection processes can be used at this stage.

The apparatus of FIG. 1 has the following advantages:

1) The stimuli will use efficiently the communication bandwidth of a cochlear implant to transmit the most salient information to the neurons to represent the acoustical signal sparsely. The stimuli generated based on this sparse version of the signal will stimulate the neurons efficiently without adding redundant stimuli. And in such a way the scheme will overcome the information bottleneck by sending the most valuable information to the auditory neurons through the limited communication bandwidth. Such sparse stimuli will also reduce the chances of channel interference, where activation of one channel also stimulates neurons close to adjacent channels, causing loss of channel resolution. The apparatus also minimises power consumption, which is important for wearable devices.
2) The electrodes will only stimulate and activate the most necessary auditory neurons for the brain to interpret the acoustical signals. Indeed this sparse transform with thresholding can be seen as a method of redundancy reduction. Redundancy reduction was the objective of sparse coding in the first place (Barlow, 1994; Field 1994).
3). By stimulating neurons sparsely, the scheme will simulate the natural physiological firing of neurons in sensory systems.
4). A consequence of redundancy reduction is that the scheme will efficiently remove contamination of the acoustical input signal.

Figure 9:
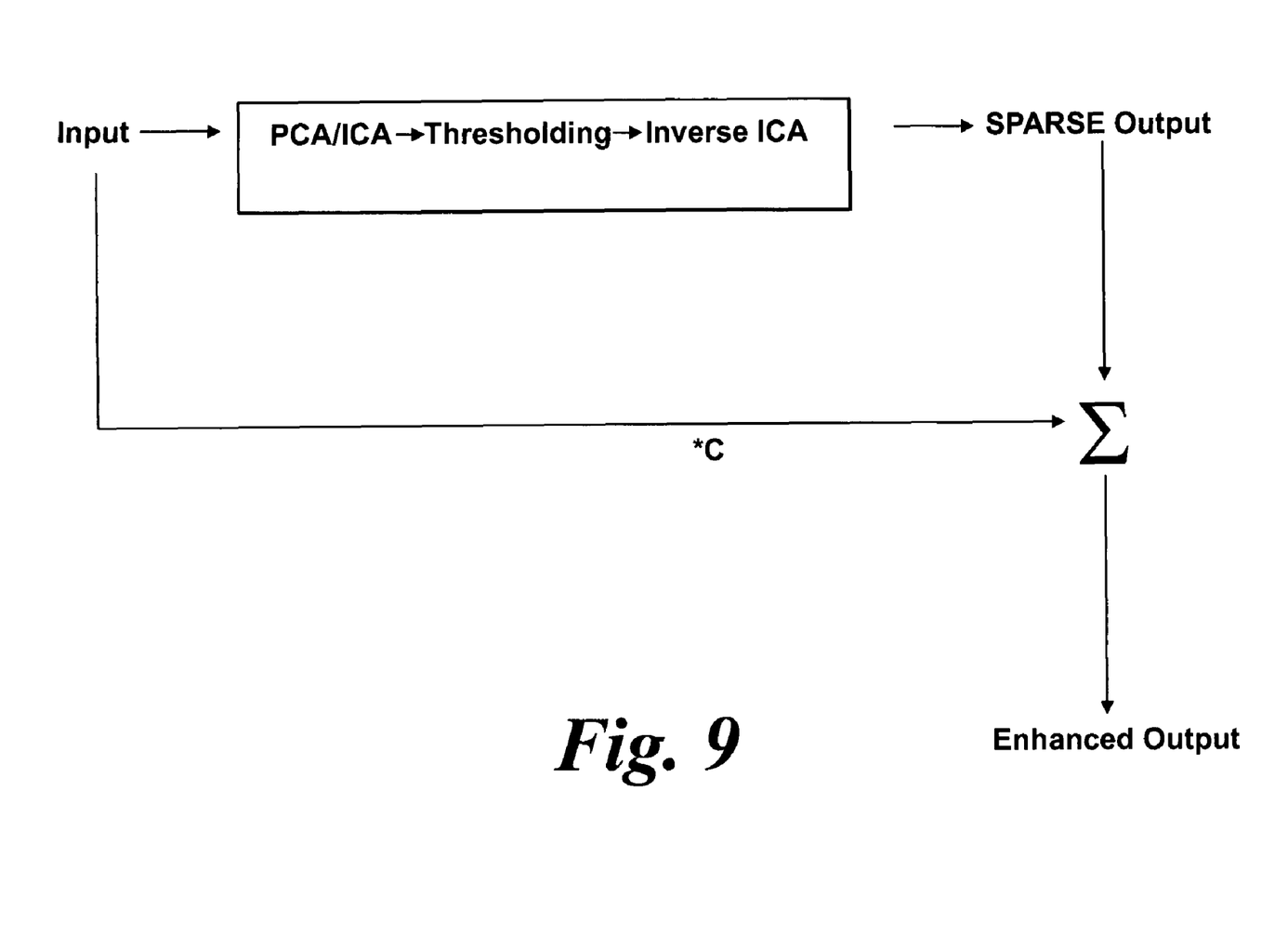
FIG. 9 shows the use of a weighted combination of the SPARSE output and the original input.

FIG. 9 shows how a weighted combination of SPARSE output and the original input may enhance the amplitude modulation and onsets of the signal.

Weighting parameter C may be set by patient adjustment or based on analysis of the signal characteristics (eg SNR).

REFERENCES

Barlow, H. (2001). "Redundancy reduction revisited." Network 12(3): 241-53.
Davies, M. (2004). "Identifiability issues in noisy ICA." Signal Processing Letters, IEEE 11(5): 470-473.
Field, D. J. (1994). "What Is the Goal of Sensory Coding." Neural Computation 6(4): 559-601.
Huang, D. S., S. Li, et al. (2006). "Noise removal using a novel non-negative sparse coding shrinkage technique." Neurocomputing 69(7-9): 874-7.
Hyvarinen, A. (1999). "Sparse code shrinkage: Denoising of nongaussian data by maximum likelihood estimation." Neural Computation 11(7): 1739-1768.
Hyvarinen, A. and E. Oja (1997). "A fast fixed-point algorithm for independent component analysis." Neural Computation 9(7): 1483-1492.

The invention claimed is:

1. An apparatus comprising:
means for receiving an incoming excitation signal having a signal spectrum to which a body part would be responsive if the body part was functioning normally;
a signal analyser configured to perform dimension reduction or factorisation of the excitation signal in the time domain or in the frequency domain followed by a sparse transform, the analyser producing a clean output signal for input to an inverse transformation step to create the sparsified signal;
means for providing electrical pulses to neurons of a deficient signal-responsive body part based on the sparsified signal,
whereby the signal analyser converts the excitation signal into a sparsified signal for electrically stimulating the neurons, thereby reducing the redundancy of the stimuli applied to the neurons by the electrical pulse means.

2. Apparatus as claimed in claim 1 in which the body part is a sensory organ.

3. Apparatus as claimed in claim 1 in which the body part is an area of the brain stem.

4. Apparatus as claimed in claim 2 in which the sensory organ is a visual sensory organ, said excitation signal being an optical signal.

5. Apparatus as claimed in claim 2 in which the sensory organ is an auditory sensory organ.

6. Apparatus as claimed in claim 5 in the form of a cochlear implant.

7. Apparatus as claimed in claim 1 in which said dimension reduction or factorisation is performed by principal component analysis (PCA).

8. Apparatus as claimed in claim 1 in which said sparse transform is performed by independent component analysis (ICA).

9. Apparatus as claimed in claim 8 in which the ICA output signal (S) is subjected to thresholding to reduce redundant components before the resulting thresholded signal is subjected to the transformation step.

10. Apparatus as claimed in claim 9 in which the maximum likelihood method is used to get the signal threshold, using a relationship of the form:

$$S\_essential' = \frac{\text{sign}(S).*\max(0, |S| - a.*\sigma^2)}{(1 + \sigma^2 * b)}$$

where S_essential corresponds to the sparse envelopes of said ICA output signal S, $\sigma^2$ is the estimated variance of the noise, and a and b are selected integers.

11. Apparatus as claimed in claim 10 in which a=3 and b=8.

12. Apparatus as claimed in claim 1 in which said dimension reduction or factorisation is performed in the frequency domain.

* * * * *